(12) United States Patent
Aksan et al.

(10) Patent No.: US 6,375,672 B1
(45) Date of Patent: Apr. 23, 2002

(54) METHOD FOR CONTROLLING THE CHEMICAL AND HEAT INDUCED RESPONSES OF COLLAGENOUS MATERIALS

(75) Inventors: Alptekin Aksan, East Lansing; John J. McGrath, DeWitt, both of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/532,327

(22) Filed: Mar. 21, 2000

Related U.S. Application Data
(60) Provisional application No. 60/125,521, filed on Mar. 22, 1999.

(51) Int. Cl.⁷ .............................. A61F 2/00; A61F 7/00
(52) U.S. Cl. ..................... 607/96; 607/101; 607/102; 606/9
(58) Field of Search .................. 607/88–89, 96, 607/98–99, 101–102; 606/13–15, 9

(56) References Cited
U.S. PATENT DOCUMENTS

| | | | |
|---|---|---|---|
| 4,544,638 A | | 10/1985 | Siegel |
| 4,911,710 A | * | 3/1990 | Milthorpe et al. ............ 623/66 |
| 5,264,551 A | | 11/1993 | Petite et al. |
| 5,458,596 A | | 10/1995 | Lax et al. |
| 5,567,806 A | | 10/1996 | Abdul-Malak et al. |
| 5,569,242 A | | 10/1996 | Lax et al. |
| 5,591,157 A | | 1/1997 | Hennings et al. |
| 5,817,144 A | | 10/1998 | Gregory |
| 5,925,078 A | * | 7/1999 | Anderson .................... 623/66 |
| 5,954,716 A | * | 9/1999 | Sharkey et al. ............... 606/32 |

OTHER PUBLICATIONS
Hayashi et al., Am. J. Sports Med. 25: 107–112 (1997).
Burkhead et al., J. Bone Surg. 74A: 890–896 (1992).
Payne et al., Clin. Sports Med. 14: 863–883 (1995).
Bana et al., Sports Med. Arthroscopy Rev. 1: 242–248 (1993).
Bigliani, Techn. Orthop. 3: 36–45 (1989).
Jobe, Techn. Orthop. 3: 29–35 (1989).
Chen and Humphrey, J. Biomechanics 31: 211–216 (1998).
Chen et al., IEEE Trans. Biomed. Eng. 45: 1234–1240 (1998).
Shaefer et al., Am. J. Sports Med. 25: 841–848 (1997).
Simionescu et al., J. Biomed. Mater. Res. 25: 1495–1505 (1991).
Gohel and Amin, J. Controlled Release 51: 115–122 (1998).
Lynn et al., J. Biomed. Mater. Res. 24: 1185–1201 (1990).
Gade et al., J. Biomed. Mater. Res. 25: 799–811 (1991).
Finger et al., Arch. Ophthalmol. 105: 716–718 (1987).
Lee et al., J. Biomed. Mater. Res. 28: 981–992 (1994).
Davidson, Conn. Tissue Res. 18: 293–305 (1989).
Naimark et al., Biorheology 35: 1–16 (1998).
Ruijrok et al., J. Mater. Sci. Mater. Med. 5: 80–87 (1994).
Horgan et al., Arc. Biochem. Biophys. 281: 21–26 (1990).

(List continued on next page.)

*Primary Examiner*—Roy Gibson
(74) *Attorney, Agent, or Firm*—Ian C. McLeod

(57) ABSTRACT

The present invention provides a method for strengthening collagen in collagenous tissue which uses the controlled application of heat to induce shrinkage or contraction of the collagen in the tissue and a cross-linking means which cross-links the shrunken collagen in the tissue thereby stabilizing and strengthening collagenous tissue. In particular, the present invention provides an in vivo method for treating joint instability problems, controlled manipulation of skin structure and properties, and other problems involving collagen-containing tissues. The present invention further provides an in vitro method for stabilizing collagenous tissue for use in vivo or in vitro. Further, the present invention provides a method for treating collagenous tissue and testing the strength and stability of the treated tissue.

42 Claims, 7 Drawing Sheets

OTHER PUBLICATIONS

Moore et al., J. Biomed. Mater. Res. 32: 209–214 (1996).
Gavilanes et al., Conn. Tissue Res. 13: 37–44 (1984).
Miles et al., J. Mol. Biol. 245: 437–446 (1995).
Wren and Carter, J. Biomech. Eng. 120: 55–61 (1998).
Olde Damink et al., J. Mater. Sci. Mater. Med. 6: 460–472 (1995).
Naseef III et al., Am. J. Sports Med. 25: 670–674 (1997).
Hayashi et al., Arthroscopy 12: 474–481 (1996).
Allain et al., Conn. Tissue Res. 7: 127–133 (1980).
Cilesiz et al., Laser Surg. Med. 21: 269–277 (1997).
Pearce et al., Proc. SPIE 1876: 180–186 (1993).
Le Lous et al., Conn. Tissue Res. 11: 199–206 (1983).
Kang et al., J. Biomech. Eng. 117: 86–93 (1995).
Privalov, Adv. in Protein Chem. 35: 1–104 (1982).
Tang et al., Laser Surg. Med. 21: 438–443 (1997).
Privalov, Ann. Rev. Biophys. Chem. 18: 47–69 (1989).
LeCarpentier, IEEE Trans. Biomed. Eng. 40: 188–199 (1993).
Chen et al., J. Biomech. Eng. 119: 372–378 (1997).
Chen et al., J. Biomech. Eng. 120: 382–388 (1998).

* cited by examiner

METHOD FOR CONTROLLING THE CHEMICAL AND HEAT INDUCED RESPONSES OF COLLAGENOUS MATERIALS

CROSS-REFERENCE TO RELATED APPLICATION

The application claims the benefit of U.S. Provisional Patent Application Serial No. 60/125,521, which was filed Mar. 22, 1999.

STATEMENT REGARDING FEDERALLY SPONSORED RESEARCH OR DEVELOPMENT

None.

BACKGROUND OF THE INVENTION (1) Field of the Invention

The present invention relates to a method for strengthening collagen in collagenous tissue which uses the controlled application of heat to induce shrinkage or contraction of the collagen in the tissue and a cross-linking means which cross-links the shrunken collagen in the tissue thereby stabilizing the strengthened, collagenous tissue. In particular, the present invention relates to an in vivo method for treating joint instability problems, controlled manipulation of skin structure and properties, and other problems involving collagen-containing tissues. The present invention further relates to an in vitro method for stabilizing collagenous tissue for use in vivo or in vitro. Further, the present invention relates to a method for treating collagenous tissue and testing the strength and stability of the treated tissue.

(2) Description of Related Art

Glenohumeral instability caused by shoulder capsular redundancy, glenohumeral joint laxity, and excessive joint volume, for example, is a problem affecting approximately 8% of the population. Kinematically, the problem may be defined as the inability to maintain the humeral head (the ball) centered in the fossa (the socket) caused by the pathological redistribution of the forces that keep the joint in equilibrium.

Redistribution of the forces are generally initiated by soft tissue problems. These can occur from a single acute event that disrupts the capsule, recurrent microtrauma that damages the biological microstructure of the joint capsule or a traumatic ligamentous laxity. The result is that the soft tissue allows for excessive motion of the joint surfaces in directions not normally permitted by the ligaments or capsule surrounding the joint.

This problem is generally seen in athletes and the young. In the milder cases, symptoms include shoulder fatigue, weakness and pain while repetitive dislocation and subluxation and even the loss of motion are indicative of more severe cases.

Currently applied treatments for glenohumeral instability include closed techniques, open techniques, and arthroscopic techniques. Closed techniques which are based on exercise depend on strengthening the muscle group that surrounds the shoulder joint. In addition to relatively long treatment period (6 to 12 months), the high reoccurrence rate limits their application as a stand alone method (Hayashi et al., Am. J. Sports Med. 25: 107–112 (1997)). The success in treatment of mild cases is only about 20% (Burkhead et al., J. Bone Surg. 74A: 890–896 (1992).

Open techniques generally involve operative procedures and the method applied depends on the type of instability, i.e., anterior, posterior or multidirectional. It has been reported that approximately 300 different operative procedures have been applied for the surgical management of instability (Zayne et al., Clin. Sports Med. 14: 863–883 (1995)). In addition to being technically difficult, these operations which are performed for the capsule shift or repair are generally known to result in pain and have the potential to reduce range of motion and even cause loss of motion, nerve injury and osteoarthritis (Bana et al., Sports Med. Arthroscopy Rev. 1: 242–248 (1993); Bigliani, Techn. Orthop. 3: 36–45 (1989); Jobe, Techn. Orthop. 3: 29–35 (1989)). Only 30% of patients undergoing surgical operations for glenohumeral instability appear to achieve their pre-injury function.

Arthroscopic techniques generally pose less risk of neuromuscular injury and typically involve a shorter rehabilitation period compared to open techniques. While arthroscopic techniques have less risk of neuromuscular injury and require a shorter rehabilitation period than other techniques, these techniques require extreme technical expertise and are very much dependent on the skill of the surgeon. Furthermore, in many cases, the repair effected by arthroscopic techniques is short-term since reoccurrence rates as high as 50% have been observed. As such, alternatives to the foregoing techniques are highly desirable.

Recently, arthroscopic thermotherapy has begun to be applied for the treatment of glenohumeral instability problems. The therapy aims to reduce the excessive capsular volume and ligamentous laxity by heating the articular surfaces of the glenoid and the humeral head, a method otherwise referred to herein as heat assisted capsular shift procedure. Arthroscopic thermotherapy techniques for contracting collagen fibers in soft tissue to increase rigidity of the tissue have been the object of several U.S. Patents.

U.S. Pat. No. 5,591,157 to Hennings et al. discloses an apparatus and method for tightening the tympanic membrane by using a laser to apply heat to the collagen fibers of the membrane. The heat causes the collagen fibers to contract which tightens the membrane.

U.S. Pat. Nos. 5,569,242 and 5,458,596 to Lax et al. discloses an apparatus and method for strengthening the collagenous tissue in the joint to stabilize the joint by the controlled contraction of the collagen tissue. The apparatus provides thermal energy to the soft tissue which causes the collagen fibers to contract or shrink thereby improving the stability of the joint.

Although results of short term follow ups show that arthroscopic thermotherapy is promising with relative few side effects, questions about the long term effect remain unanswered. Improved range of motion of the repaired shoulder, accelerated patient healing, as well as lower recurrence rates are the major advantages of this therapy. The disadvantages are the time dependent decrease of tissue stiffness, over-stiffening or excessive drop in tissue strength in cases of overexposure to heating, and the trend for relaxation of the treated tissue back to its untreated length. This kind of response has also been observed in most of the research done using animal models (Chen and Humphrey, J. Biomechanics 31: 211–216 (1998); Chen et al., IEEE Trans. Biomed. Eng. 45: 1234–1240 (1998); Shaefer et al., Am. J. Sports Med. 25: 841–848 (1997)). Time-dependent changes in the mechanical properties and behavior of the treated tissue are thought to be the major reason for recurrence and thus, failure of the therapy in the long run. A further disadvantage with currently proposed arthroscopic thermotherapy is that the success of the therapy completely depends on subjective parameters such as the visual perception, experience, and judgment of the surgeon. Thus, while arthroscopic thermotherapy appears to be an advancement in the art, understanding the phenomena involved in tissue response is incomplete and because of recurrence, improvements are clearly needed.

There are other methods known in the art for modifying collagen. For example, chemical modification of collagen films and collagenous tissues using cross-linking agents such as glutaraldehyde, 1-ethyl-3-(3-dimethylaminopropyl)-carbodiimide, hexamethylene diisocyanate and diphenylphosphorylazide which induce inter/intramolecular bonds have been used for fixation in histological examinations (Simionescu et al., J. Biomed. Mater. Res. 25: 1495–1505 (1991)), controlled drug release (Gohel and Amin, J. Controlled Release 51: 115–122 (1998)), delaying the in vivo degradation of (Lynn et al., J. Biomed. Mater. Res. 24: 1185–1201 (1990)), and suppressing the recipient immune response (Gade et al., J. Biomed. Mater. Res. 25: 799–811 (1991)) to soft tissue xenografts like porcine heart valves and arteries. On the macro scale, the effects of these modifications are known to be pronounced with respect to viscoelastic behavior and mechanical properties like stiffness and toughness (Finger et al., Arch. Ophthalmol. 105: 716–718 (1987); Lee et al., J. Biomed. Mater. Res. 28: 981–992 (1994); Davidson, Conn. Tissue Res. 18: 293–305 (1989); Naimark et al., Biorheology 35: 1–16 (1998)) as well as with respect to the denaturation temperature (Ruijrok et al., J. Mater. Sci. Mater. Med. 5: 80–87 (1994); Horgan et al., Arc. Biochem. Biophys. 281: 21–26 (1990); Moore et al., J. Biomed. Mater. Res. 32: 209–214 (1996); Gavilanes et al., Conn. Tissue Res. 13: 37–44 (1984)).

Chemical modification of collagen fibers using cross-linking agents has been the object of several U.S. Patents. U.S. Pat. No. 5,567,806 to Abdul-Malak et al. discloses using cross-linking agents in the manufacture of suturable, biocompatible slow-resorbing membranes which can be used for guided tissue regeneration. U.S. Pat. No. 5,264,551 to Petite et al. discloses a process for cross-linking collagen in articles intended for implantation in a patient using diphenylphosphorylazide which provides the ability to modulate the biodegradability of the collagen depending on the degree of cross-linking. U.S. Pat. No. 4,544,638 to Siegel discloses a process for introducing cross-links in the helical domain of collagen using pyridoxal 5-phosphate and copper or iron. The process is designed to reintroduce into processed collagen the native cross-linking which provides the native collagen its high tensile strength and resistance to degradation and resorption.

However, chemical cross-linking has not been used in the treatment of glenohumeral instability problems or loose skin problems, and in particular, chemical cross-linking has not been used in conjunction with thermotherapy.

SUMMARY OF THE INVENTION

The present invention provides a method for treating collagenous tissue wherein both the mechanical properties and the stability of the collagenous tissue are improved over current methods. In one embodiment, the present invention provides an improved arthroscopic thermotherapy method wherein a curing solution containing one or more cross-linking agents is used in combination with the controlled heat administration to the collagenous tissue or after the controlled administration of heat to the collagenous tissue. When heat is applied to the collagenous tissue, the native cross-links in the collagen are disrupted which causes the collagen to denature and thus to contract and shrink. A cross-linking means is provided which cross-links the contracted collagen thereby maintaining the collagen in the contracted form. Cross-linking the contracted collagen improves the mechanical properties of the collagenous tissue because it abrogates the time-dependent decrease of tissue stiffness and/or tensile strength and by modifying the viscoelastic response so as to prevent the contracted collagen to relax back to its untreated length. In the manner supra, the present invention improves the safety and reliability of thermotherapy procedures, in particular, Heat-Assisted Capsular Shift procedures which are used to repair joint injuries of the shoulder, elbow, wrist, hand, spine, neck, hip, knee, and ankle. In an other embodiment, the present invention provides a method for treating loose skin by tightening up the skin with heat treatment to the collagen therein followed by treatment with a cross-linking means which stabilizes the tightened skin. The method is useful for removing wrinkles and sagging skin caused by old age, and sagging skin caused by over-stretching or prolonged stretching of the skin.

Thus, the present invention provides a stabilizing treatment of collagenous tissue in vivo in a mammal which comprises providing an energy source to the collagenous tissue to heat the collagenous tissue, heating the collagenous tissue for a time sufficient to contract collagen comprising the collagenous tissue, and treating the contracted collagenous tissue with a non-toxic cross-linking means which cross-links the contracted collagen wherein the cross-linked contracted collagen stabilizes the collagenous tissue. In particular, the collagenous tissue comprising internal body parts selected from the group consisting of shoulder, elbow, wrist, hand, spine, neck, hip, knee, and ankle, or the collagenous tissue comprising skin.

In the method of the present invention, the cross-linking means is a chemical cross-linking agent or a photo-fixing means with or without a dye. Preferably, the chemical cross-linking agent is selected from the group consisting of glutaraldehyde, 1-ethyl-3-(3-dimethylaminopropyl)-carbodiimide, hexamethylene diisocyanate, diphenylphosphorylazide, and mixture of pyridoxal-5-phosphate and cupric or ferrous ion. Further, in the method of the present invention, the energy is preferably provided by a source selected from the group consisting of a laser, an electrode which provides a radiofrequency energy, ultrasound, an alternating magnetic field, microwaves, and heated aqueous solution.

The present invention further provides a system for a stabilizing treatment of collagenous tissue in vivo which comprises a heating means for heating the collagenous tissue so that collagen comprising the collagenous tissue is contracted, and a dispensing means for introducing a non-toxic cross-linking means into contact with the collagenous tissue so that the contracted collagen is stabilized.

Further still, the present invention provides an in vitro or in vivo method for treating tissue, in particular collagenous tissue, to stabilize the collagen therein which comprises providing heat to tissue containing the collagen wherein the collagen is contracted because of being heated, and treating the contracted collagen with a cross-linking means which cross-links the contracted collagen so that the contracted collagenous tissue is stabilized.

In particular embodiments of the system for treatment and the in vivo or in vitro method of treatment supra, the treatment is to the collagenous tissue comprising internal body parts selected from the group consisting of shoulder, elbow, wrist, hand, spine, neck, hip, knee, and ankle, or the collagenous tissue comprising skin. In an embodiment further still, the treatment is accomplished arthroscopically.

In the system for treatment or the in vitro or in vivo method of treatment supra, the cross-linking means is a chemical agent which is preferably selected from the group consisting of glutaraldehyde, 1-ethyl-3-(3-dimethylaminopropyl)-carbodiimide, hexamethylene diisocyanate, diphenylphosphorylazide, and mixture of pyridoxal-5-phosphate and cupric or ferrous ion or a photo-fixing means with or without a dye, and it is preferable that the heating means is selected from the group consisting of a laser, an electrode which provides a radiofrequency energy, ultrasound, alternating magnetic field, microwaves, and heated aqueous solution.

The present invention further provides an apparatus for treatment of tissue to stabilize collagen therein which comprises a holding means for mounting the tissue to be treated, a heating means for heating the tissue to contract the collagen therein, and a dispensing means for introducing a cross-linking agent into contact with the contracted collagen which cross-links the collagen, thereby stabilizing the contracted collagen in the tissue which increases its mechanical strength.

Further still, the present invention provides a system for testing stabilizing treatments on collagenous tissue which comprises: an apparatus comprising a holding means for mounting the tissue to be treated, an energy means for heating the tissue to contract collagen therein, a dispensing means for introducing a cross-linking means into contact with the contracted collagen which cross-links the collagen thereby stabilizing the contracted collagen in the tissue, and a testing means for testing mechanical properties of the tissue before, during and after treatments.

In particular embodiments of the apparatus or system of the present invention, the dispensing means provides the cross-linking agent to the tissue in a field and the heating means is selected from the group consisting of a laser, an electrode which provides a radiofrequency energy, ultrasound, alternating magnetic field, microwaves, and heated aqueous solution. In particular embodiments, the cross-linking means is a chemical agent which is preferably selected from the group consisting of glutaraldehyde, 1-ethyl-3-(3-dimethylaminopropyl)-carbodiimide, hexamethylene diisocyanate, diphenylphosphorylazide, and mixture of pyridoxal-5-phosphate and cupric or ferrous ion or a photo-fixing means with or without a dye.

The apparatus and system supra are particularly useful for treating or testing collagenous tissue comprising internal body parts selected from the group consisting of shoulder, elbow, wrist, hand, spine, neck, hip, knee, and ankle, or the collagenous tissue comprising skin.

Objects

Therefore, it an object of the present invention to provide a method and system for providing increased mechanical strength and stability of collagenous tissue. In particular, it is an object of the present invention to provide a method that enables the long-term repair of joint problems and loose skin problems.

These and other objects will become increasingly clear with reference to the following preferred embodiments, examples and drawings.

DESCRIPTION OF PREFERRED EMBODIMENTS

The main structural element of cartilaginous tissues like tendon, joint capsule, ligament and skin is the collagen molecule. Tropocollagen molecules, which are made up of three collagen molecules ($\alpha$-chains) wound about each other making a collagen triple-helix, are bonded in a head-to-tail pattern to form tropocollagen trains which are then bonded or cross-linked to each other in a parallel pattern to form collagen fibrils. A parallel arrangement of these fibrils form the collagen fibers (shown in FIG. 1). This well organized, hierarchical structure enforced by the inter/intramolecular and inter/intrafibrillar chemical bonds (cross-links) determines the response of the tissue to various stimuli (Miles et al., J. Mol. Biol. 245:437–446 (1995); Wren and Carter, J. Biomech. Eng. 120:55–61 (1998); Olde Damink et al., J. Mater Sci. Mater. Med. 6: 460–472 (1995)). The intermolecular cross-links provide collagen connective tissue with high tensile strength and substantial elasticity. Collagen connective tissue is ubiquitous in mammals, e.g., humans, and demonstrates several characteristics not found in other tissues. It provides the cohesiveness of the musculoskeletal system, the structural integrity of the viscera as well as the elasticity of the integument. There are basically five types of collagen molecules; Type I is most common in bone, tendon, skin, and other connective tissues, and Type III is common in muscle and elastic tissues.

Figure 1:
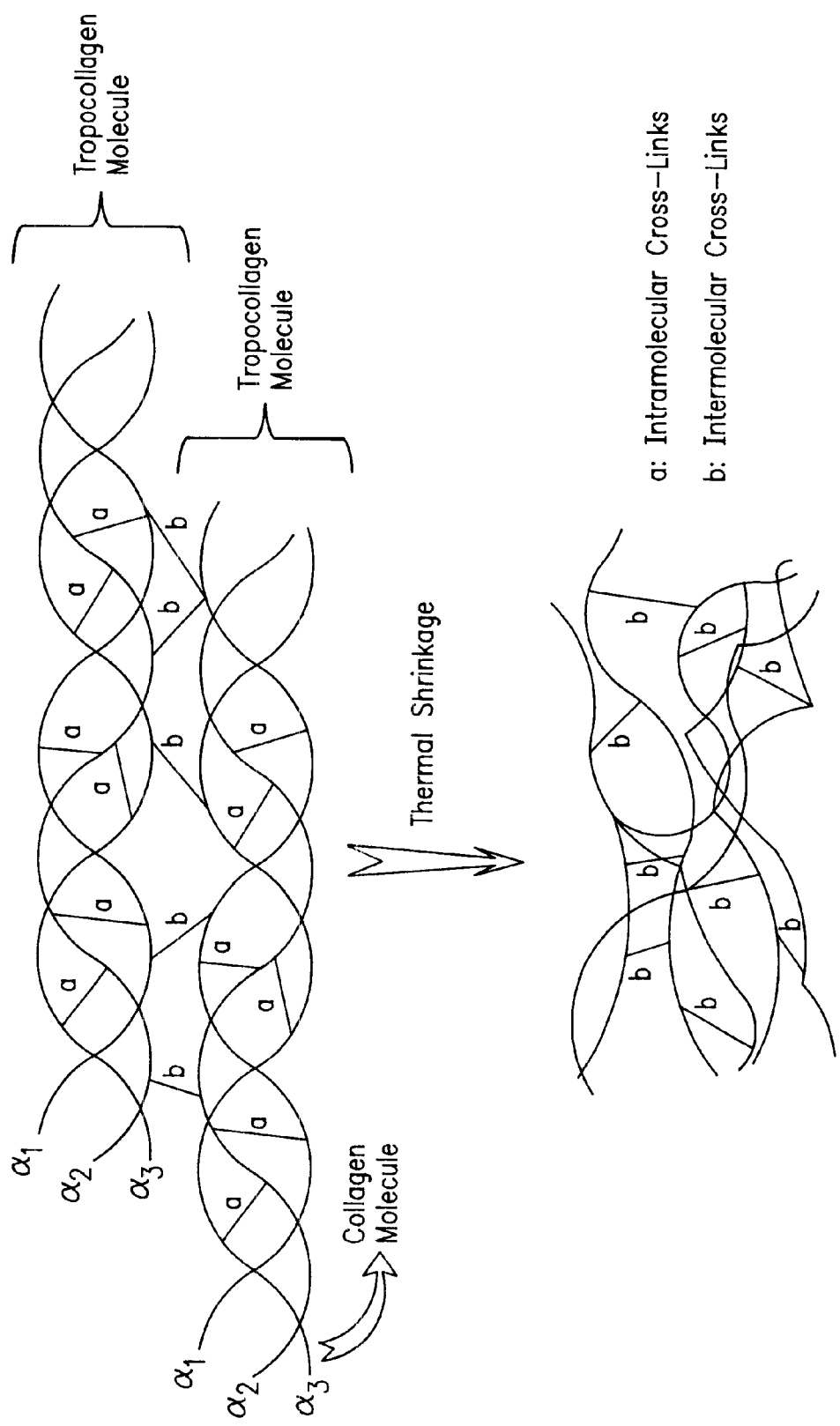
FIG. 1 is a schematic view of thermal induced shrinkage of tropocollagen molecules.
Figure 2:
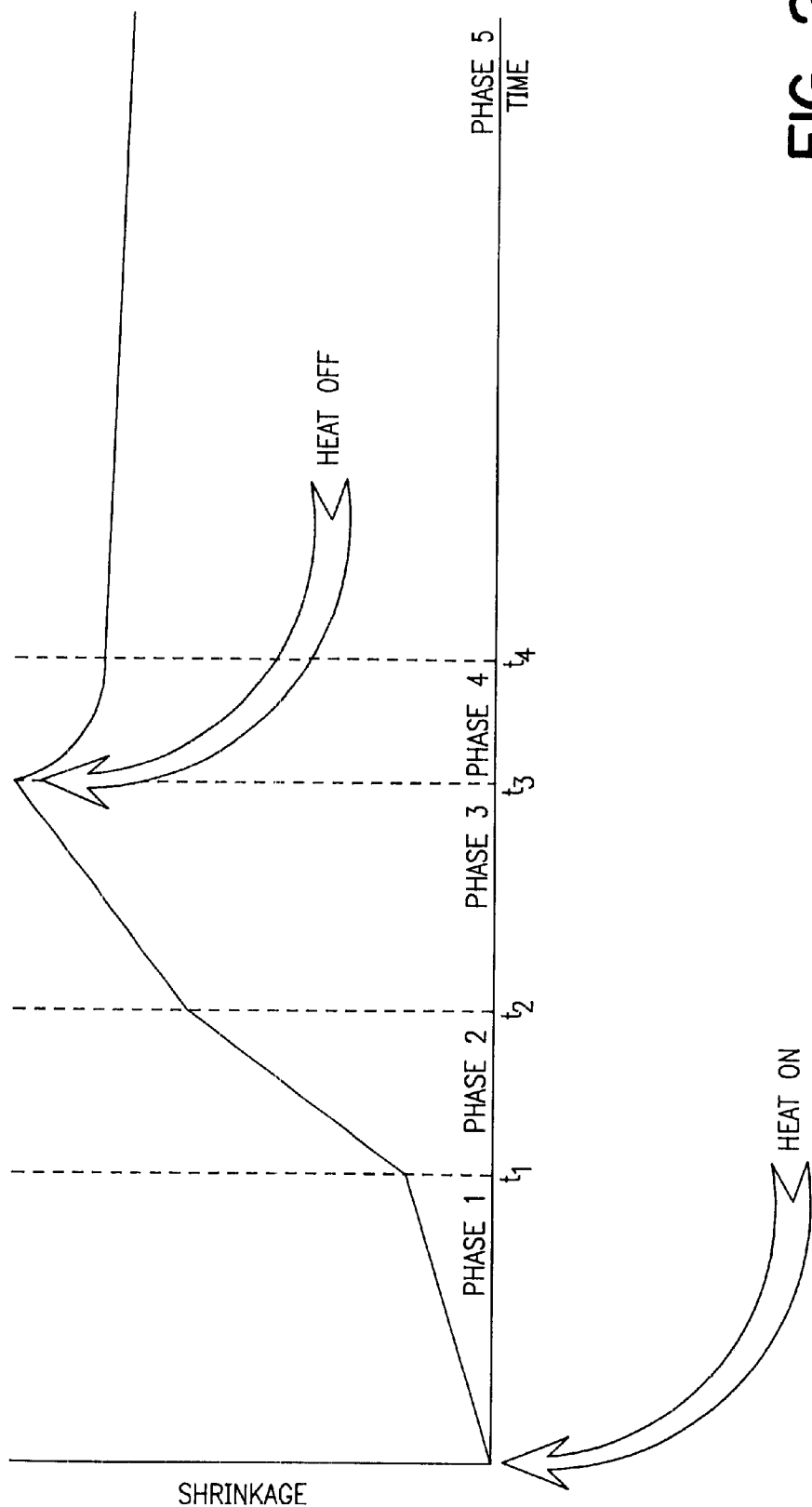
FIG. 2 is a graph showing isothermal shrinkage of bovine chordae tendineae during application of heat. Graph is based on Chen et al., IEEE Trans. Biomed. Eng. 45: 1234–1240 (1998).

A previously recognized property of collagen is shrinkage of collagen fibers when the tissue is elevated in temperature. When heat is applied to collagen fibers, their highly oriented parallel structure is denatured or transformed to an amorphous state because the helical tropocollagen molecules lose the harness of their heat-labile intramolecular bonds as illustrated in FIG. 1. At the macroscopic scale, the result is tissue shrinkage as illustrated in FIG. 2. This molecular response to temperature elevation causes the immediate contraction of the collagen fibers to about one-third of their lineal distention. When the tissue is allowed to cool back to its initial neutral state temperature, relaxation from shrinkage and gradual renaturation back to its native or near-native configuration is observed. The rate of relaxation and extent of renaturation depend on the tissue and the extent of heat denaturation of the collagen in the tissue. Although shrinkage in response to various heating processes for different collagenous tissues has been well documented, a consensus on the magnitude and irreversibility of thermomechanical strain formation and the effects of environmental, non-thermal factors has not yet been reached.

As used herein the effect of heat on collagen fibers is described as causing denaturation, contraction, or shrinkage of the collagen fibers. These terms are used interchangeably herein to describe the effect of heat on the collagen fibers and it is not to be construed that use of one of the above descriptive terms is to preclude the other descriptive terms. For example, heat disrupts the inter- and intramolecular cross-links in the collagen fiber which denatures the collagen molecules comprising the fiber. Because the collagen molecules collapse in on themselves and the collagen molecules comprising the fibrils of the fiber are attached to the tissue, the denatured collagen causes the fiber to shrink or contract, which in turn causes the tissue containing the fibers to shrink or contract as well. Thus, when the contracted collagenous tissue comprise the capsule surrounding a joint, the capsule, because of its reduced size and its enhanced geometric and dynamic stability, is better able to resist joint dislocation wherein the bone of the joint slips out of the joint.

Collagenous tissue denaturation or shrinkage in response to heating by laser, microwave, radiofrequency devices, and hydrothermy is an extensively studied phenomena (Naseef III et al., Am. J. Sports Med. 25: 670–674 (1997); Hayashi et al., Arthroscopy 12: 474–481 (1996); Allain et al., Conn. Tissue Res. 7: 127–133 (1980)). The amount and the extent of irreversibility of tissue shrinkage, i.e., thermomechanical strain formation, depends on many factors, including the maximum temperature reached and the exposure time (Miles et al., J. Mol. Biol. 245: 437–446); Cilesiz et al., Laser Surg. Med. 21:269–277 (1997); Pearce et al., Proc. SPIE 1876: 180–186 (1993); Le Lous et al., Conn. Tissue Res. 11: 199–206 (1983)), the mechanical stress applied on the tissue during heating (Kang et al., J. Biomech. Eng. 117: 86–93 (1995), the surrounding fluid chemistry, e.g., pH and electrolyte concentration (Privalov, Adv. in Protein Chem. 35: 1–104 (1982), as well as the type of collagen (Tang et al., Laser Surg. Med. 21: 438–443 (1997), its hydration level (Privalov, Ann. Rev. Biophys. Chem. 18: 47–69 (1989), and the degree of the cross-linking (Olde Damink et al., J. Mater. Sci. Mater. Med. 6: 460–474 (1995); Ruijgrok et al., J. Mater. Sci. Mater. Med. 5: 80–87 (1994)). In other words, the coupled effects of the amount and rate of heat deposition, the properties of the tissue, and the surrounding medium govern the response on both the microscopic and macroscopic levels (LeCarpentier, IEEE Trans. Biomed. Eng. 40: 188–199 (1993).

The heat-induced responses of collagenous tissue under isothermal, stress-free, and isotonic shrinkage conditions have been quantified recently for a bovine model under hydrothermal heating conditions (Chen and Humphrey, J. Biomech. 31: 211–216 (1998); Chen et al., IEEE Trans. Biomed. Eng. 45: 1234–1240 (1998); Chen et al., J. Biomech. Eng. 119: 372–378 (1997); Chen et al., J. Biomech, Eng. 120: 382–388 (1998)). These studies have revealed that the heat-induced denaturation of collagenous tissue, expressed in terms of thermomechanical strain formation, can be quantified by a single Arrhenius-type relationship which depends on the temperature, the exposure time, and the mechanical stress that is applied to the tissue. This finding together with the differentiation of different thermo-mechanical response regimes (denaturation phases) are considered in establishing a model of the tissue thermal response. As shown in FIG. 2, for the isothermal heating protocol applied, generally, three different shrinkage phases are distinguishable: a linear pre-transition phase, a non-linear transition phase, and a linear post-transition phase. The mechanisms responsible for these different shrinkage phases and their relationship to thermal and mechanical modifications in the tissue are not understood.

Methods for contracting or shrinking collagen fibers in collagenous tissue using an energy source have been disclosed in U.S. Pat. Nos. 5,569,242 and 5,569,242 to Lax et al., U.S. Pat. No. 5,591,157 to Hennings et al. and methods for applying laser energy to a particular site within a body lumen was disclosed in U.S. Pat. No. 5,817,144 to Gregory. In the method of the present invention, any one of the above is suitable as the means for inducing the shrinkage, contraction, or denaturation of the collagen fibers in the tissue to be repaired. Accordingly, the aforementioned U.S. Patents are hereby incorporated herein by reference.

Figure 3:
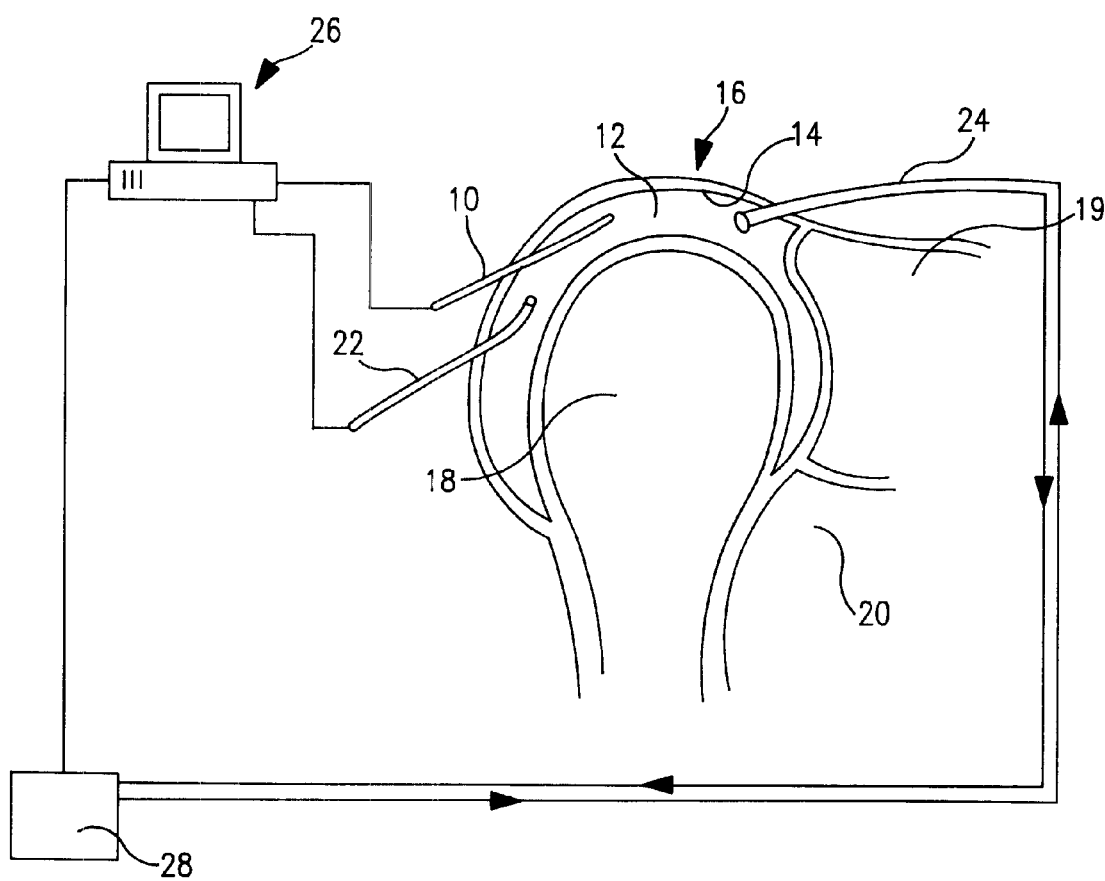
FIG. 3 is a schematic illustration of chemical and Heat Assisted Capsular Shift procedures on the capsule of the shoulder joint.

According to the present invention, providing any one of a number of cross-linking agents during Heat Assisted Capsular Shift or skin tightening procedures can improve the long-term thermomechanical response of collagenous tissues. In particular, cross-linking agents can be applied during (in the form of arthroscopic fluids) or following (as curing solutions) thermotherapy to irreversibly fix shrinkage as illustrated in FIG. 3. By performing the cross-linking step during or following the heat-denaturation step, relaxation of the shrunken collagen fibers from the heat shrunken state is reduced or substantially abrogated thereby improving the stability and strength of the tissue following the treatment. The improvement in stability is longer-term than that which can be obtained by using heat alone, which while improving the stability of the tissue does not provide the long-term strengthening effect that is provided by the present invention. The improvement in the strength and stability of the tissue is significant when compared to cross-linking alone, which provides a long-term effect but because the tissue was not contracted or shrunken does not increase the stability of the tissue.

Examples of cross-linking agents which are suitable for practicing the present invention include, but are not limited to, glutaraldehyde, 1-ethyl-3-(3-dimethylaminopropyl)-carbodiimide, hexamethylene diisocyanate, diphenylphosphorylazide, and mixture of pyridoxal-5-phosphate and cupric or ferrous ion. Alternatively, the cross-linking can be achieved by providing photo-fixing means with or without a dye. Aqueous glutaraldehyde solutions consist of a mixture of free aldehyde, mono- and dihyrated monomeric glutaraldehyde, monomeric and polymeric cyclic hemiacetals and various alpha, beta, unsaturated polymers which are equilibrium. Glutaraldehyde reacts primarily with amino groups, generating thermally stable cross-links. In an advantageous embodiment, the heat treated collagen is treated at a temperature that is preferably within the range of 37° and 85° C. with a solution containing about 0.1 to 1.0% glutaraldehyde in phosphate buffered saline at pH 7.4. The treatment is between about a minute and an hour. In a preferred embodiment, the treatment is for 15 minutes. Afterwards, the excess glutaraldehyde is removed by washing with phosphate buffered saline, pH 7.4. Optionally, the wash can include a blocking agent (0.025M glycine solution) which inactivates any unreacted glutaraldehyde.

Diphenylphosphorylazide induces cross-linking of collagen by forming amide bonds by means of acylazide groups. In an advantageous embodiment, the heat treated collagen is treated with a borate buffer of a pH about 8.9 and at a temperature between about 40° C. to 60° C. The length of the treatment can be from between a few hours, and about one day. Methods for use and parameters to consider for the use of diphenylphosphorylazide is disclosed in U.S. Pat. No. 5,567,806 to Abdul-Malak et al. and U.S. Pat. No. 5,264,551 to Petite et al. which are hereby incorporated herein by reference.

A mixture of pyridoxal-5-phosphate and cupric or ferrous ion induces cross-linking by converting the amide group in the side chain of lysine or hydroxylysine moieties in the collagen helix to the corresponding aldehyde. These lysyl or hydroxylysyl aldehydes are then capable of cross-linking with other converted lysyl or hydroxylysyl residues in a Schiff base reaction, thus cross-linking adjacent collagen chains. The initial reaction is probably a Schiff base with pyridoxal. The by-product of the cross-linking reaction is water. The preferred temperature for cross-linking is between about 37° C. and 60° C. The reaction is maintained at a roughly neutral pH, i.e., 6 to 7, preferably pH 6.4. The reaction is allowed to continue for between about several hours and a day, preferably between about 2 and 24 hours. Methods for using pyridoxal-5-phosphate and cupric or ferrous ions is disclosed in U.S. Pat. No. 4,544,638 to Siegel which is hereby incorporated herein by reference.

The present invention operates under the premise that the controlled administration of heat and cross-linking agents during joint repair procedures, e.g., Heat-Assisted Capsular Shift procedures, and other procedures such as those for treating loose skin can be used to modify in a beneficial manner the long-term mechanical response of the treated or repaired tissue. This is expected to result in an increase in the success rate for the above procedures and enhance the long-term stability of the repaired tissue. In particular, it is envisioned that the cross-linking agents are to be applied to tissue being repaired, preferably in the form of arthroscopic fluids to the tissue during the thermotherapy procedure which irreversibly fixes the shrinkage, contraction, or denaturation of the collagen fibers in the tissue. Alternatively, the cross-linking agents are applied to the heat-treated tissue following the thermotherapy, as a curing solution which irreversibly fixes the shrinkage, contraction, or denaturation of the collagen fibers in the tissue. Thus, the present invention minimizes or substantially abrogates the relaxation over time of the contracted collagen fibers from the heat shrunken or contracted form.

Therefore, the present invention provides an improved method for treating a patient with a joint instability disorder such as a glenohumeral instability disorder caused by capsular redundancy, glenohumeral joint laxity, and excessive joint volume. FIG. 3 illustrates operation of the heat and cross-link method of the present invention in a procedure for the arthroscopic repair of the soft collagen tissue forming the joint capsule of the shoulder joint of a patient. A probe 10 which provides an energy source that delivers heat, e.g., laser, electrical, radiofrequency, light, microwave, alternating magnetic field, or equivalent means for generating heat, is introduced into glenoid cavity 12 of joint 20 between soft collagen tissue 14 comprising joint capsule 16, ball of the humerus 18, and scapula 19, and is painted across the surface of soft collagen tissue 14. Wherever probe 10 is painted, the heat delivered causes contraction of the collagen fibers in collagen tissue 14. The extent of contraction in any particular area of the heat treated soft collagen tissue 14 is directly proportional to the length of time the heat is applied to the particular area. The contracted collagen fibers in collagen tissue 14 produces a collagen tissue that is contracted or shrunken, which increases the geometric stability of the joint 20. The more stable capsule provides a wider range of motion to the patient without causing joint dislocation. Optionally, an arthroscopic camera 22 is provided which enables the operator to observe the arthroscopic procedure. The cross-linking agent from source 28 is introduced into glenoid cavity 12 by means of an arthroscopic fluid supply line 24. The cross-linking agent is provided either as a component of arthroscopic fluid or as a solution which is pharmaceutically acceptable for arthroscopic procedures, either during the heat treatment or concurrently with application of the heat, or the cross-linking agent is provided subsequent to the heat treatment as a component of a curing solution. The degree of cross-linking of the heat contracted collagen is related to the concentration of cross-linker in the solution, the length of time the cross-linker containing solution is provided to the collagen tissue, and the temperature at which the cross-linking solution is provided to the glenoid cavity. Arthroscopic supply line 24 also provides a means for removal of the cross-linking agent, and for adding a cross-linking blocker from source 28 which inactivates unreacted blocker, and for washing by providing fluid from source 28 which replaces fluid containing cross-linker and/or blocker. Alternatively, cross-linking can be achieved by photo-fixing wherein light of a particular wavelength that causes cross-linking of the collagen fibers in the collagen tissue is provided with or without a dye.

The cross-linked contracted collagen fibers in the collagen tissue have enhanced strength compared to contracted collagen fibers that have not been cross-linked. The increased stability means that the arthroscopic treatment according to the present invention has a longer lasting effect than methods for treating glenohumeral instability that do not provide cross-linking. Therefore, a patient who has been treated according to the present invention maintains the beneficial results of the treatment for a longer time period before the patient needs a second arthroscopic procedure. Thus, the frequency of arthroscopic treatments necessary to maintain the range of motion for the joint desired by the patient is reduced. Optionally, in the above method, a system is provided wherein probe 10, source 28 which provides cross-linker, blocker, and other fluids to the site by arthroscopic fluid supply line 24, and arthroscopic camera 22 are connected to a central processing unit 26 which regulates the heat produced by probe 10 and controls the amount, duration, temperature, and removal of cross-linker provided by arthroscopic fluid supply line 24, thereby facilitating the treatment. The temperature of the above fluids is controlled by a heating means (not shown). While the above relates to treatment of glenohumeral instability problems of the shoulder joint, it would be readily apparent to one skilled in the art that the above treatment procedure can be applied to the treatment of other joint problems, such as those affecting the elbow, wrist, hand, spine, neck, hip, knee, and ankle.

The present invention is also intended to be a treatment for loose skin problems wherein the heat and cross-link procedure tightens the skin thereby substantially reducing the extent or degree of skin looseness. In general, looseness of the skin develops during aging and/or over-stretching, i.e., if the skin has been stretched beyond its elastic recovery point such that when the cause of the stretching has been removed, the skin does not recover from the stretching but remains loose. Examples of over-stretched loose skin includes skin that has been over-stretched by pregnancy and remains loose after birth; skin that has been over-stretched by obesity and remains loose after removal of the underlying fatty tissue by weight loss or liposuction; skin that has been stretched by means of an implant and that remains stretched after removal of the implant, e.g., an implant containing silicon, saline, or other material which has been used for breast enlargement or muscle-definition enhancement; skin that has become loose because the underlying muscle mass has atrophied due to old age, disuse, or disease; and overstretched skin attaching the breast to the chest caused by aging and/or the exertion of gravitational forces on the breast. Treatment of the above loose skin or over-stretched skin conditions is generally performed for cosmetic reasons.

In the prior art, loose skin is usually removed by surgical methods wherein a portion of the loose skin is removed and the remaining skin is stretched tightly to cover the area that was removed, e.g., face-lift procedures to remove facial wrinkles or skin removal procedures to remove excess skin after the underlying fatty tissue has been removed. The disadvantage of such surgical techniques is that the result is not long-lasting. In addition, because the skin has been pulled tightly, it is thinner than it had been before the procedure. Another disadvantage is that the tightened skin will eventually become loose, and to maintain the desired wrinkle-reduced appearance, the surgical procedure is repeated to remove the newly developed loose skin. Thus, after several of the above surgical procedures, the skin is substantially thinner than it would have been if the skin had not been tightened. Another disadvantage is that the surgical procedure is an invasive medical operation requiring anesthesia and presents the risk of disfigurement or even death.

Therefore, the present invention provides a method for providing cosmetic treatments to a patient without resorting to cosmetic surgery and thereby incurring its attendant disadvantages. According to the method of the present invention, the loose skin is treated with sufficient heat to cause the collagen in the skin tissue to contract thereby tightening the skin. The tightening causes the wrinkles or other loose skin to be substantially reduced. Cross-linking is then induced by providing the cross-linking agent in a solution which is then applied to the heat-shrunken skin either topically, by injection, or by a method which enables the subcutaneous application of the cross-linking agent. The cross-linking of the contracted collagen provides stability to the contracted collagen as well as resulting in increased mechanical strength of the collagen and renders the effect of the treatment long-term. An advantage of the present invention is that the tightening of the skin does not result in a thinning of the skin. Therefore, in contrast to the surgical procedures, multiple skin tightening procedures to the same region of the skin using the method of the present invention does not result in a gradual thinning of the skin. Another advantage of the present invention is that it is not an invasive medical operation and, therefore, it can be performed on an out-patient basis. It is expected that the method of the present invention is particularly suitable for face-lift procedures and for tightening skin after removing the fat under the skin following procedures such as liposuction. The present invention can further be used in conjunction with collagen injection procedures which are used for removing facial wrinkles.

While the present invention provides a means for avoiding cosmetic surgery, under particular circumstances, cosmetic surgery is unavoidable, i.e., the skin is so loose that treatment exclusively by the present invention will not achieve the desired skin tightening. Therefore, in those circumstances, the present invention is used in conjunction with cosmetic surgery wherein the amount of skin that is surgically removed is only the amount that is necessary to provide the desired cosmetic effect after treatment according to the present invention. Thus, a cosmetic effect is achieved which has the benefits that are conferred by the present invention and a substantial reduction of the disadvantages that are inherent in cosmetic surgery procedures. Furthermore, subsequent treatments need only be performed according to the present invention.

According to the present invention, to establish clinically applicable and acceptable therapy protocols for controlling the thermomechanical response of soft tissues the following are considered. The mechanisms governing heat-induced tissue response and tissue thermal damage are specified and quantified by examining the relative effects of mechanical stress, thermal history, maximum temperature reached, and exposure time on the irreversibility of thermal and mechanical modification, i.e., thermomechanical damage, and the correlation between these two phenomena. Thus, for each type of collagenous tissue, it is necessary to examine and quantify the coupled effects of tensile stress, maximum temperature reached, time of exposure, and properties of the surrounding medium on the extent of reversibility and irreversibility of thermal modification. It is also important to understand the relationships among the types and properties of the cross-links and quantify their effects on the macroscopic scale. The properties of the cross-links include location (intra/intermolecular and intra/interfibrillar), heat response (heat-lability or heat-resistance), and structure (mechanical or chemical significance). This enables the various aspects of the cross-links and their effects on gross tissue behavior to be distinguished.

The above enable construction of a mathematical model for collagenous tissues which couples the chemical, mechanical, and thermal phenomena and tissue structure, including the effects of collagen fiber orientation and inter-molecular cross-linking density distribution of the tissue which enables determining the effect of these parameters on the heat-induced denaturation phases and viscoelastic properties of the tissue. Thus, specific therapy protocols using chemical cross-linking agents concurrent with or subsequent to heat therapy are developed to manipulate and control the tissue thermomechanical responses to particular joint injuries.

Figure 4:
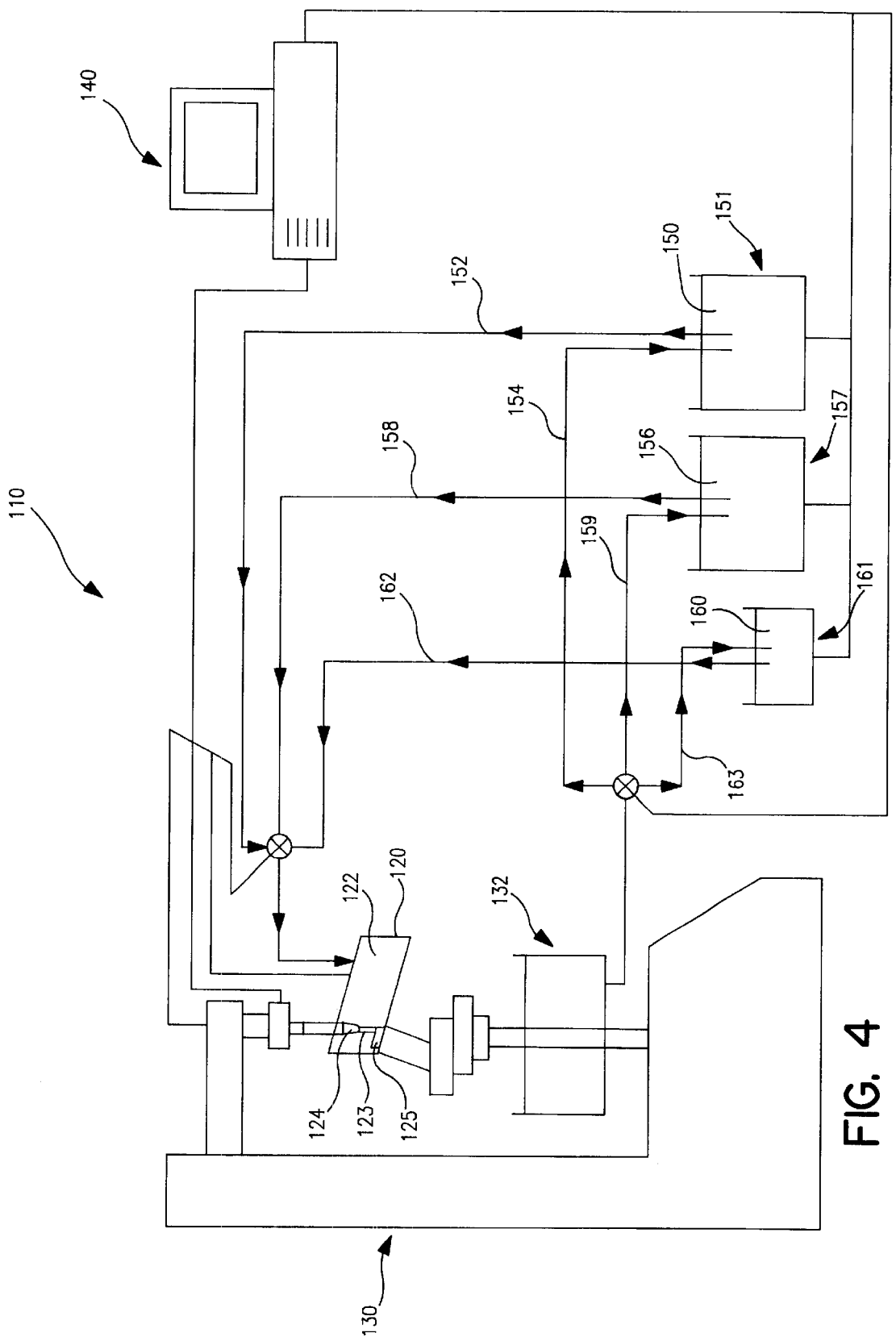
FIG. 4 is a schematic illustration of a system utilized to carry out testing procedures related to the process of the present invention.

The achieve the above objectives, the present invention provides an in vitro testing system for developing procedures for treating joint instability problems and loose skin problems. In particular, the testing system performs a tensile test, which is a test wherein a constant rate of elongation is applied on the specimen and the resultant load is measured by a load cell; a viscoelasticity test, which is a test to determine the viscoelastic properties of the specimen; and, calculates stiffness which is the slope of elongation versus load graph. The testing system 110 is illustrated in FIG. 4 and consists of a hydrothermy cabin 120 that is attached to a universal testing machine 130, which is used to perform isothermal and isotonic heating of specimens. The hydrothermy cabin 120 provides a chamber which allows fluid to be circulated around all surfaces of specimen 123 held in between lower grip 124 and upper grip 125. Specimen 123 is secured to lower grip 124 using a fixture which is designed to keep specimen 123 at an angle to mimic anatomical loading while compensating for the offset created by the angle so as to ensure a straight line of loading. Specimen 123 is secured to upper grip 125 by a wedge-shaped fixture which is composed of two universal joints to give rotational freedom to specimen 123 to ensure that a purely uniaxial stress is created on specimen 123. The denaturation of the collagen in specimen 123 is produced by providing to hydrothermy cabin 120 high temperature saline solution 150 contained in reservoir 151 by means of high temperature saline solution supply line 152. During this process, the solution is continuously circulated by being collected in collector 132 and returned to reservoir 151 by return line 154. Next, cross-linking solution 156 is provided by cross-linking solution supply line 158, circulated in hydrothermy cabin 120, collected in collector 132 and returned back to reservoir 157 via the cross-linking solution return line 159. The extent of cross-linking is controlled by exposure time of cross-linking, concentration of cross-linker, temperature of cross-linking solution 156, and by the amount of stress on specimen 123. Intermolecular cross-links are introduced while the specimen is under constant stress whereas intramolecular cross-links are introduced applying the same protocols under cyclic loading conditions in the universal testing machine 130. The relative movement of the collagen fibers with respect to each other caused by continuous reciprocating movement by the cyclic loading pattern is presumed to prevent or minimize intermolecular cross-link formation. Next, cross-linking blocker solution 160 contained in reservoir 161 is provided by supply line 162, circulated inside hydrothermy cabin 120, collected in collector 132 and returned back to the reservoir 161 via blocker solution return line 163. Mechanical testing of the treated specimen is by operation of the materials testing machine 130 which applies displacement on the treated specimen and measures the load formed. The materials testing machine 130 performs a tensile test wherein a constant rate of elongation is applied to specimen 123 and the resultant load is measured by a load cell (not shown); a viscoelasticity test wherein a constant load is applied on specimen 123 and the resultant elongation as a function of time is measured (creep test) or a constant elongation is imposed and the resulting load is measured (stress relaxation test) as a function of time. The tensile test enables calculation of stiffness which is the slope of the elongation versus load graph. Measurements of the ultimate tensile strength are also taken. A control and data acquisition system 140, which is used to perform, measure, and record uni-axial displacement measurements, includes a central processing unit such as a personal computer and data acquisition boards. Control system 140 also controls the temperature of denaturation solution 150, cross-linking solution 156, and blocker solution 160 by a heating means for each of the above solutions; circulation of the solutions inside the hydrothermy cabin 120 and, thus the length of time specimen 123 is exposed to each of the solutions; and, manipulation of specimen 123 by 130 during application of each of the solutions.

Quantitative histological analysis to determine the cross-linking density distribution including nondestructive, birefringence analysis, and polarized microscopy, as well as destructive determination of the unreacted lysine groups of the tested samples is performed using standard histological procedures and fluorescence microscopy. The distribution of collagen fiber orientation is quantified using Fourier Transform Analysis of the collected images. The differences between selectively cross-linked tissues is used to quantify the relationship among structure, mechanical and thermal properties. The effects of exposure temperature, heating time, environmental pH, and the ratio of inter/intramolecular cross-link formation for various cross-linking agents and cure conditions as well as the mechanical load applied are other variables which are considered for purposes of defining optimal procedures. Finally, the test groups are statistically compared to each other and a correlation among the parameters defining the heat induced response are determined.

The above testing system 110 is also useful for treating in vitro various collagen-containing biomaterials which are intended to be used in transplant procedures. Examples of biomaterials intended for transplanting into mammals include, but are not limited to, bioprosthetic valves, vascular prostheses, and tissue replacements like tendons, ligaments and bones for mammals. The degree of cross-linking modulates the biodegradability of the collagen in the biomaterial, which enhances the life-span of the biomaterial in the mammal as well as modifying the immune response. The above testing system is also useful for producing biomaterials containing collagen which are to be used as supports (or substrates) for growth of material such as skin in culture or as skin grafts.

The following example is intended to promote a further understanding of the present invention.

EXAMPLE 1

New Zealand rabbit patellar tendons were used in the experiments to demonstrate the feasibility of the present invention. The rabbit patellar tendon complexes, which are composed of the patella, the patellar tendon, and the tibia, were harvested immediately after sacrifice. The muscle groups and fat surrounding the tendon tissue were removed, and the complex was wrapped in gauze soaked with a phosphate buffered saline solution at neutral pH. The wrapped patellar tendon complex specimens were stored at a temperature below $-100°$ C. until testing.

Before the experiment, the specimens were thawed overnight at $4°$ C. and then immersed in a phosphate buffered saline solution at room temperature. The specimens were stored in the saline solution for short-term storage. Before the experiment, the geometrical dimensions of the tendon were measured using a micrometer. After the measurements the tibia was inserted into an aluminum tube. Holes were drilled in two locations and steel pins were used to fix the bone to the tube. Further stability was accomplished by filling the tube with an inert glue.

Then, the aluminum tube encasing the tibia was secured to the lower grip of the materials testing system using a custom-made fixture. The fixture was designed so that the specimen would be kept at an angle to mimic anatomic loading. The fixture was also capable of compensating for the offset created so as to ensure a straight line of loading.

The patella was secured to the upper grip of the materials testing system using another custom designed wedge-shaped fixture. The upper fixture was composed of two universal joints to give rotational freedom to the specimen to ensure that a purely uniaxial stress was created on the specimen.

The hydothermy cabin was placed around the specimen and then secured to the lower fixture. A small load on the order of 1 Newton (N) was applied to the specimen before the mechanical preconditioning protocol was activated.

Before the main experiment was started, mechanical preconditioning was applied on the specimen in order to minimize the initial visco-elastic effects. The mechanical preconditioning protocol is summarized as follows. First, a load of 1.5 N was applied on the specimen in a load controlled fashion and kept constant for ten seconds while the displacement was allowed to vary. Second, a sinusoidal excitation step at an amplitude of 0.5 mm was applied at a frequency of 1 Hz for 10 cycles. Third, another load controlled step was applied wherein the specimen was kept at 1.5 N for an additional 10 seconds. Fourth, a ramp loading step was applied wherein the load on the specimen was increased to the test load level calculated for each specimen based on the sample cross-sectional area. The test load varied for all specimens since the aim was to create equal stress on each specimen.

After the mechanical preconditioning, the load test was performed. During the test, the test load was kept constant by running the materials testing machine in a load controlled mode so that the displacement was allowed to vary with the changes in the length of the specimen. The following data were obtained in the experiments: the load on the specimen, the change in the displacement of the grips, and the temperature of the specimen as well as the temperature of the baths. The data was collected at a rate of not less than 10 Hz and recorded.

Initially, high temperature phosphate buffered saline solution at a constant test temperature of 75° C. or 80° C. was circulated inside the hydrothermy cabin for a period of 300 to 500 seconds (the thermal treatment protocol) depending on the experiment group. After the first protocol was deactivated, the specimen was subjected to a glutaraldehyde cross-linking agent at a concentration of either 0.1% or 0.5% (the chemical treatment protocol) for a period of time sufficient to achieve adequate penetration and cross-linking of the agent, about 15 minutes. In a control group, the specimen was subjected to a phosphate buffered saline solution. After the chemical treatment protocol was completed, the third-cycle deactivation protocol was started. During this protocol, a cross-linking blocker agent (0.025M glycine solution) was circulated throughout the hydrothermy cabin for 900 seconds at room temperature. The neutralizing agent reacted with the free cross-linking agent thereby neutralizing it and preventing any further cross-linking in the specimen. After 900 seconds of cross-linking blocker agent circulation, a tension test at a rate of 0.25 mm per second was performed until the specimen failed.

Figure 5:
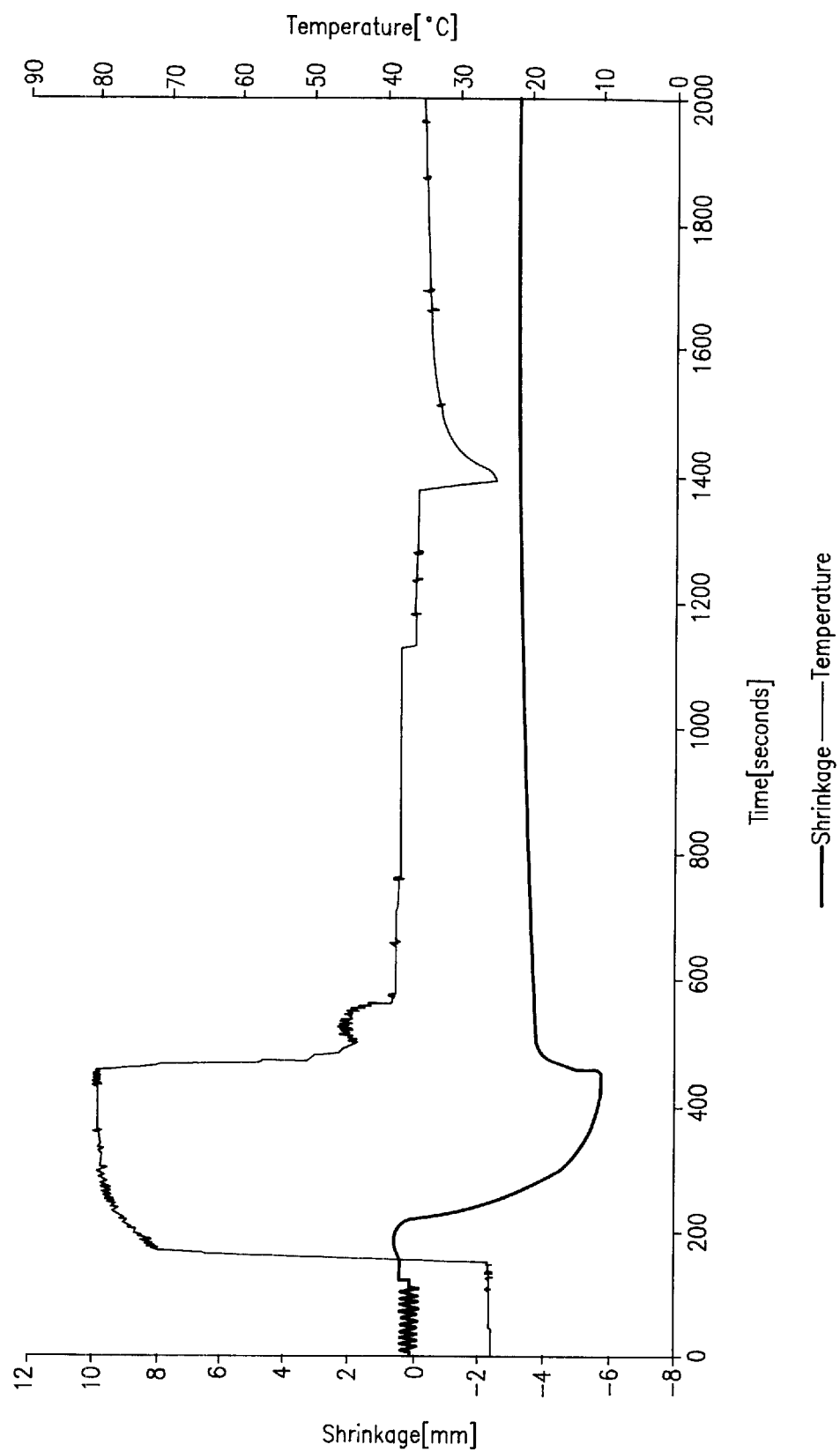
FIG. 5 shows the shrinkage of a rabbit patellar tendon specimen with temperature over time.
Figure 6:
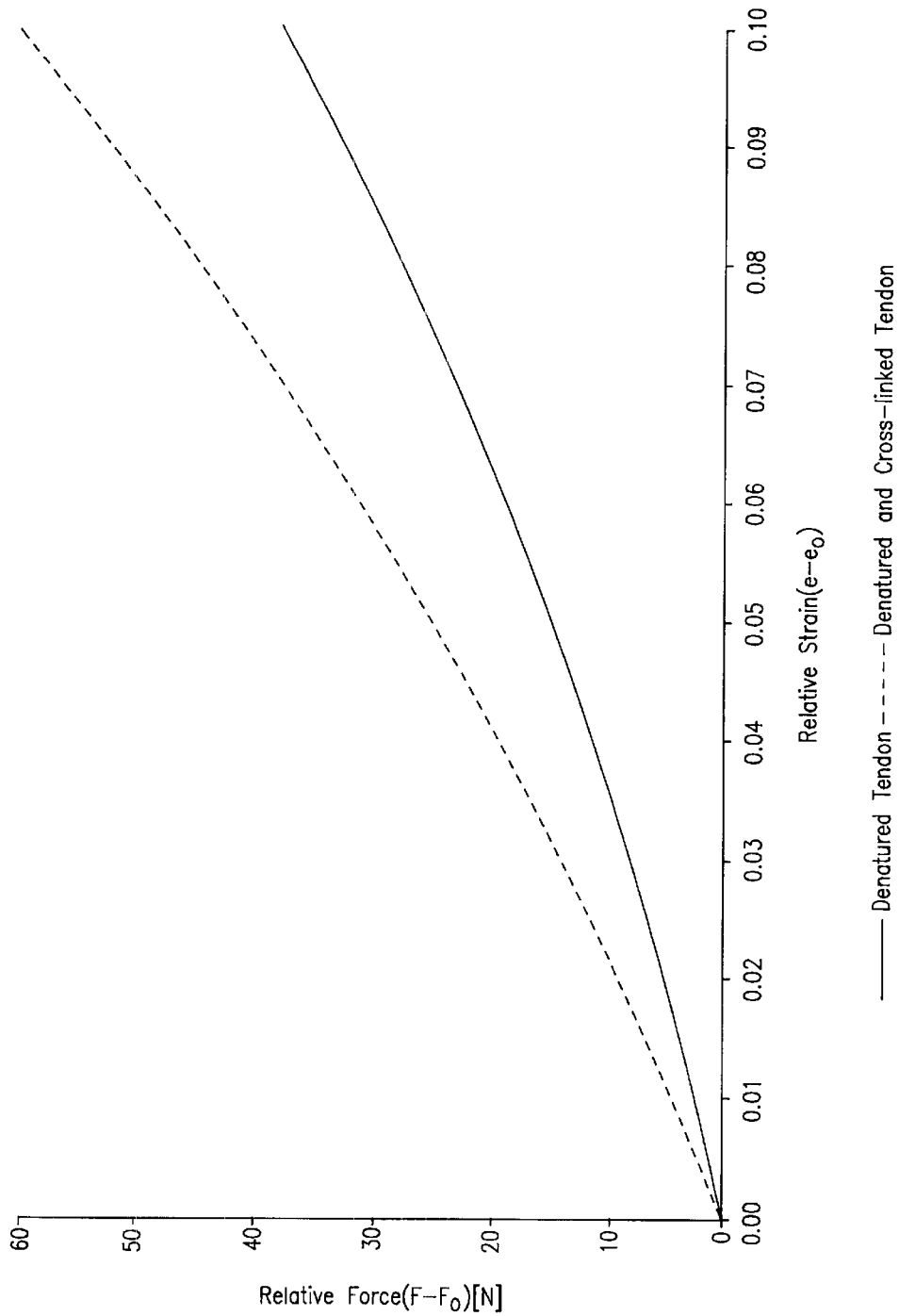
FIG. 6 shows the results of a tension test comparing the stiffness values of the cross-linked and uncross-linked tendon of a rabbit patellar tendon specimen after thermal denaturation. The values of strain and force are referenced with respect to their respective values before the tension test is started.
Figure 7:
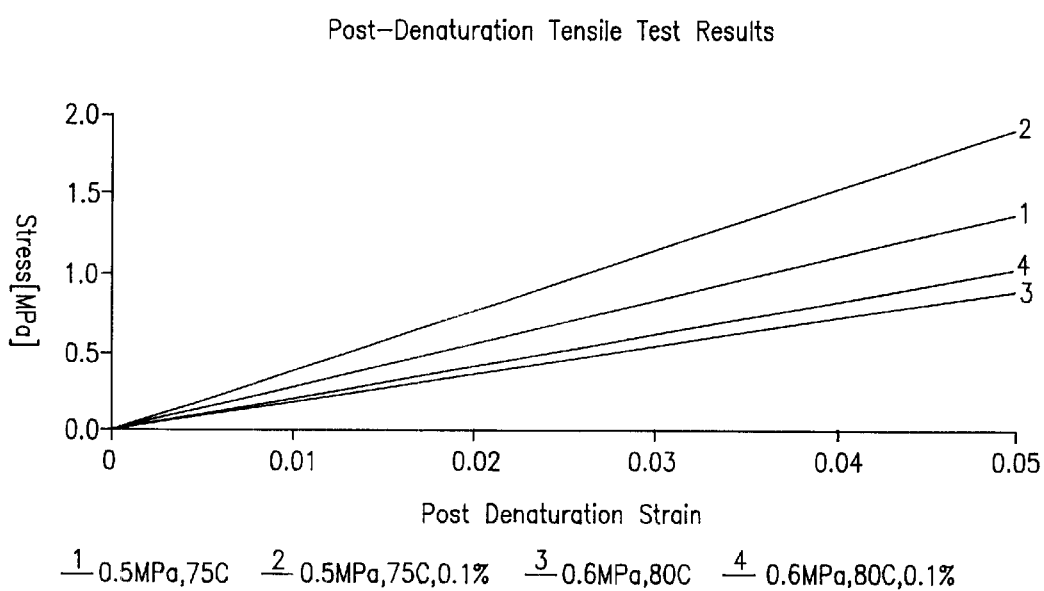
FIG. 7 shows the post-denaturation tensile test results of rabbit patella specimens wherein the collagen had been contracted by heat at 75° C. or 80° C. and the contracted collagen stabilized with either 0.1% glutaraldehyde or no glutaraldehyde.

The results are shown in FIGS. 5 to 7. FIG. 5 shows the shrinkage of the specimen over time and temperature. FIG. 6 shows the results of a tension test which compared the stiffness values of the cross-linked and uncross-linked tissues after thermal denaturation. As shown in FIG. 6, the denatured and cross-linked specimen had greater stiffness than the denatured but uncross-linked specimen. Thus, the method of the present invention provides greater stiffness to treated tissue than tissue treated merely by heat denaturation. FIG. 7 shows that after 15 minutes of 0.1% glutaraldehyde treatment following a heat treatment of either 75° C. or 80° C., the stiffness of the specimen had increased. In the specimen treated at 75° C. and subjected to 0.5 MPa load, the stiffness was increased by more than 220% when compared to a control without the cross-linking. In the specimen treated at 80° C. and subjected to a 0.6 MPa load, the stiffness was increased by more than 130% when compared to a control without the cross-linking.

The results of the experiments confirmed that the heat induced responses and shrinkage of collagen films and-tissues can be controlled by employing certain cross-linking agents in various forms, before, after, or simultaneously with the application of heat as illustrated in FIG. 3.

After the testing, the specimens were removed from the fixture, flash frozen in liquid nitrogen and stored at −100° C. for histological examination. Histological examinations were to determine the amount of cross-linking agent penetration, and the degree of thermal denaturation achieved during the test.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A method for producing a stiffened and stabilized collagenous tissue in vivo in a mammal which comprises:
    (a) providing an energy source to the collagenous tissue to heat a collagenous tissue at a temperature sufficient to denature collagen within the collagenous tissue;
    (b) heating the collagenous tissue with the energy source at the temperature for a time sufficient to denature the collagen within the collagenous tissue to produce a contracted collagenous tissue; and
    (c) treating the contracted collagenous tissue with a non-toxic cross-linking means to produce the stiffened and stabilized collagenous tissue.

2. The method of claim 1 wherein the cross-linking means is a chemical agent or a photo-fixing means and a dye.

3. The method of claim 2 wherein the chemical agent is selected from the group consisting of glutaraldehyde, 1-ethyl-3-(3-dimethylaminopropyl)-carbodiimide, hexamethylene diisocyanate, diphenylphosphoryl azide, and mixture of pyridoxal-5-phosphate and cupric or ferrous ion.

4. The method of claim 1 wherein the energy is provided by a source selected from the group consisting of a laser, an electrode which provides a radiofrequency energy, ultrasound, alternating magnetic field, microwave, and heated aqueous solution.

5. The method of claim 1 wherein the stiffening and stabilizing is accomplished arthroscopically.

6. The method of claim 1 wherein the collagenous tissue comprises internal body parts selected from the group consisting of shoulder, elbow, wrist, hand, spine, neck, hip, knee, and ankle.

7. The method of claim 1 wherein the collagenous tissue comprises skin.

8. A system for producing a stiffened and stabilized collagenous tissue in vivo which comprises:
    (a) heating means for heating a collagenous tissue at a temperature sufficient to denature collagen in the collagenous tissue to produce a contracted collagenous tissue; and
    (b) dispensing means for introducing a non-toxic cross-linking means into contact with the contracted collagenous tissue to produce the stiffened and stabilized collagenous tissue.

9. The system of claim 8 wherein the cross-linking means is a chemical agent or a photo-fixing means and a dye.

10. The system of claim 9 wherein the chemical agent is selected from the group consisting of glutaraldehyde, 1-ethyl-3-(3-dimethylaminopropyl)-carbodiimide, hexamethylene diisocyanate, diphenylphosphoryl azide, and mixture of pyridoxal-5-phosphate and cupric or ferrous ion.

11. The system of claim 8 wherein the energy is provided by a source selected from the group consisting of a laser, an electrode which provides a radiofrequency energy, ultrasound, alternating magnetic field, microwave, and heated aqueous solution.

12. The system of claim 8 wherein the stabilizing treatment is accomplished arthroscopically.

13. The method of claim 8 wherein the collagenous tissue comprises internal body parts selected from the group consisting of shoulder, elbow, wrist, hand, spine, neck, hip, knee, and ankle.

14. The method of claim 8 wherein the collagenous tissue comprises skin.

15. The system of claim 8 wherein the heating means and the cross-linking means are controlled by a central processing unit.

16. The system of claim 8 or 15 wherein an arthroscopic camera is provided for observing the treatment.

17. A method for treating a tissue containing collagen to stiffen and stabilize the tissue containing the collagen which comprises:
    (a) providing the tissue containing the collagen wherein the tissue containing the collagen has been heated to produce a tissue with contracted collagen; and
    (b) treating the tissue with the contracted collagen with a cross-linking means which cross-links the contracted collagen in the tissue to produce the stiffened and stabilized collagenous tissue.

18. The method of claim 17 wherein the collagen is in collagenous tissue of a living animal.

19. The method of claim 17 wherein the cross-linking means is a chemical agent or a photo-fixing means and a dye.

20. The method of claim 19 wherein the chemical agent is selected from the group consisting of glutaraldehyde, 1-ethyl-3-(3-dimethylaminopropyl)-carbodiimide, hexamethylene diisocyanate, diphenylphosphoryl azide, and mixture of pyridoxal-5-phosphate and cupric or ferrous ion.

21. The method of claim 17 wherein the collagen fibers are treated in vitro.

22. The method of claim 17 wherein the collagen fibers are treated in vivo.

23. The method of claim 17 wherein the energy is provided by a source selected from the group consisting of a laser, an electrode which provides a radiofrequency energy, ultrasound, alternating magnetic field, microwave, and heated aqueous solution.

24. The method of claim 17 wherein the collagenous tissue comprises internal body parts selected from the group consisting of shoulder, elbow, wrist, hand, spine, neck, hip, knee, and ankle.

25. The method of claim 17 wherein the collagenous tissue comprises skin.

26. An apparatus for treatment of a tissue to stiffen and stabilize the tissue which comprises:
    (a) holding means for mounting the tissue to be treated;
    (b) energy means for heating the tissue to denature the collagen wherein to produce a contracted collagen in the tissue; and
    (c) dispensing means for introducing a cross-linking means into contact with the contracted collagen which cross-links the collagen to stiffen and stabilize the tissue.

27. The apparatus of claim 26 wherein the dispensing means provides the cross-linking agent to the tissue in a field.

28. The apparatus of claim 26 wherein the energy means is from a source selected from the group consisting of a laser, an electrode which provides a radiofrequency energy, ultrasound, alternating magnetic field, microwave, and heated aqueous solution.

29. The apparatus of claim 26 wherein the cross-linking means is a chemical agent or a photo-fixing means and a dye.

30. The apparatus of claim 29 wherein the chemical agent is selected from the group consisting of glutaraldehyde, 1-ethyl-3-(3-dimethylaminopropyl)-carbodiimide, hexamethylene diisocyanate, diphenylphosphoryl azide, and mixture of pyridoxal-5-phosphate and cupric or ferrous ion.

31. The apparatus of claim 26 wherein the tissue comprises internal body parts selected from the group consisting of shoulder, elbow, wrist, hand, spine, neck, hip, knee, and ankle.

32. The apparatus of claim 26 wherein the tissue comprises skin.

33. A system for testing a stiffening and stabilizing treatment on a collagenous tissue which comprises:
    an apparatus comprising a holding means for mounting the collagenous tissue, an energy means for heating the collagenous tissue to contract collagen therein, a dispensing means for introducing a cross-linking means into contact with the contracted collagen in the collagenous tissue which cross-links the collagen thereby stabilizing the contracted collagen in the collagenous tissue, and a testing means for testing mechanical strength of the stiffened and stabilized collagenous tissue.

34. The system of claim 33 wherein the dispensing means provides the cross-linking agent to the tissue in a field.

35. The system of claim 33 wherein the energy means is from a source selected from the group consisting of a laser, an electrode which provides a radiofrequency energy, ultrasound, alternating magnetic field, microwave, and heated aqueous solution.

36. The system of claim 33 wherein the cross-linking means is a chemical agent or a photo-fixing means and a dye.

37. The system of claim 36 wherein the chemical agent is selected from the group consisting of glutaraldehyde, 1-ethyl-3-(3-dimethylaminopropyl)-carbodiimide, hexamethylene diisocyanate, diphenylphosphoryl azide, and mixture of pyridoxal-5-phosphate and cupric or ferrous ion.

38. The apparatus of claim 33 wherein the tissue comprises internal body parts selected from the group consisting of shoulder, elbow, wrist, hand, spine, neck, hip, knee, and ankle.

39. The apparatus of claim 33 wherein the tissue comprises skin.

40. A system for a stabilizing treatment of collagenous tissue in vivo which comprises:
    (a) heating means for heating the collagenous tissue so that collagen comprising the collagenous tissue is contracted;
    (b) dispensing means for introducing a non-toxic cross-linking means into contact with the collagenous tissue so that the contracted collagen is stabilized; and
    (c) a central processing unit for controlling the heating means and the cross-linking means.

41. A method for tightening loose skin and stabilizing the tightened skin in vivo in a mammal which comprises:
    (a) providing an energy source to the loose skin to heat collagen fibers in the skin at a temperature sufficient to denature the collagen fibers in the skin;
    (b) heating the loose skin with the energy source at the temperature for a time sufficient to denature the collagen fibers in the skin to produce a tightened skin; and
    (c) treating the tightened skin with a non-toxic cross-linking means which stabilizes the tightened skin.

42. A method for stiffening and stabilizing a capsule surrounding a joint in vivo in a mammal to enable the joint to resist joint dislocation which comprises:
    (a) providing an energy source to the capsule surrounding the joint for heating collagen fibers in the capsule at a temperature sufficient to denature the collagen fibers therein;
    (b) heating the capsule surrounding the joint with the energy source at the temperature for a time sufficient to denature the collagen fibers in the capsule to produce a contracted capsule surrounding the joint; and
    (c) treating the contracted capsule surrounding the joint with a non-toxic cross-linking means which stabilizes the contracted capsule surrounding the joint to enable the capsule to resist joint dislocation.

* * * * *